United States Patent [19]

Yoshida et al.

[11] Patent Number: 4,594,245

[45] Date of Patent: Jun. 10, 1986

[54] AUGMENTING FACTORS FOR HUMAN ANTIBODY PRODUCTION AND PROCESS FOR PEPARING THE SAME

[75] Inventors: Takato Yoshida; Soichi Haraguchi; Teruaki Hongo; Yukio Koide, all of Hamamatsu, Japan

[73] Assignee: Hamamatsu University School of Medicine, Hamamatsu, Japan

[21] Appl. No.: 573,616

[22] Filed: Jan. 25, 1984

[30] Foreign Application Priority Data

Jul. 25, 1983 [JP] Japan ................. 58-134502

[51] Int. Cl.[4] .................. A61K 35/18; C07K 15/06; C12N 5/02; C12P 21/00
[52] U.S. Cl. .................................. 424/101; 435/68; 435/241; 514/2; 514/8; 530/351; 530/387
[58] Field of Search ............... 235/68, 240, 241; 424/101; 260/112 B; 514/2, 8

[56] References Cited

U.S. PATENT DOCUMENTS 4,001,080  1/1977  Goust et al. ................. 435/241
4,132,776  1/1979  Jeter ............................ 424/101
4,390,623  6/1983  Frabricius et al. ........... 435/68

OTHER PUBLICATIONS

Cohen et al, Inhibition of Migration of Tumor Cells in Vitro by Lymphokine-Containing Supernatants, J. of Immunology (1978) 121: 840–843.

Neville et al, Activation of Fc Receptor-Bearing Lymphocytes, by Immune Complexes, J. Immunol., 128: 1063–1068 (1982).

*Primary Examiner*—Thomas G. Wiseman
*Assistant Examiner*—Elizabeth C. Weimar
*Attorney, Agent, or Firm*—Burns, Doane, Swecker & Mathis

[57] ABSTRACT

Augmenting factors for human antibody production having a molecular weight of 2,000–4,000 are prepared from the supernatant of cultured human lymphocytes. Nylon wool-adherent cells of human lymphocytes are separated from nylon wool-passed cells, and are then cultured, dialyzed and lyophilized. The factors espeically augment and enhance the production of immunoglobulins, IgG and IgM.

7 Claims, No Drawings

AUGMENTING FACTORS FOR HUMAN ANTIBODY PRODUCTION AND PROCESS FOR PEPARING THE SAME

BACKGROUND OF THE INVENTION

1. Field of the Invention

The present invention relates to new augmenting factors for human antibody production and a process for preparing the same.

More particularly, the present invention relates to augmenting factors for human antibody production, which are prepared by human lymphocytes and which augment and enhance the production of immunoglobulins, IgG and IgM and the process for preparing the factors.

2. Description of the Prior Art

Concerning the factors for augmenting and enhancing the antibody production, many reports have been made. Among them, T-cell growth factor (Interleukin 2, IL-2), B-cell growth factor (BCGF), B-cell differentiation factor (BCDF), Interleukin 1 (IL-1) etc., are known as soluble factors produced from T-cell or macrophage. It has been found that any material having these functions is a high molecular compound having a molecular weight of 15,000–18,000 to 12,000–18,000.

Treatment and prophylaxis of diseases by using antigen-antibody reactions have obtained many good results. Nevertheless, many unsolved problems yet remain. Several incurable diseases are known by the fact that the antibody production is insufficient or too weak. In such a case, it will be expected that desired effects are obtained if the antibody production is augmented and enhanced. Such diseases include, for example, cancer, influenza, and other immunodeficiency diseases. Accordingly, the search has continued for new augmenting factors for human antibody production and processes for preparing the same.

SUMMARY OF THE INVENTION

One object of the present invention is to provide augmenting factors for human antibody production having physicochemical and biological properties as mentioned hereinafter.

Another object of the present invention is to provide a process for preparing the augmenting factors for human antibody production.

In one aspect of the present invention, in the course of studies of regulation mechanisms of human antibody formation, the inventors have found that nylon wool-adherent lymphocytes which had previously removed macrophages have remarkably augmented the antibody production.

In another aspect, the present invention includes culturing the nylon wool-adherent lymphocytes to identify the presence of low molecular weight materials for augmenting the antibody production in the culture supernatant and collecting the materials having the above functions.

Another aspect comprises dividing nylon wool-adherent lymphocytes from nylon wool-passed lymphocytes; and collecting the factors passed through a dialysis membrane from culture supernatant.

Other objects, aspects and advantages of the present invention will become apparent to one skilled in the art from the following:

DESCRIPTION OF THE PREFERRED EMBODIMENTS

The present invention includes processes for preparing augmenting factors for human antibody production (if necessary for sake of brevity and clarity hereinafter, the augmenting factors are referred to as "the present factors").

For preparing the present factors, firstly, the human lymphocytes are cultured. In order to obtain the human lymphocytes, tonsils, spleens, thymus and peripheral blood are used as the material. As an embodiment, tonsils are sliced into small pieces with a pair of curved scissors. The pieces are suspended in culture medium supplemented with pencillin, streptomycin and others, which supplemented medium protects bacterial contamination.

The cell culture medium to be used may be any marketed solution such as those trade named RPMI-1640 (Nissui Seiyaku Co., Ltd., Japan) MEM culture solutions, DMEM culture solution or 199 culture solution. Typically, each culture medium is supplemented with fetal calf serum (or human AB type serum), L-glutamine, 2-mercaptoethanol and antibiotics such as penicillin and streptomycin. These standard mediums may be further modified as desired.

The sliced tissues suspended in the cell culture medium are filtered through gauze, etc. to remove the tissue slices and obtain a cell suspension. This cell suspension is placed on Ficoll-Paque (Pharmacia Fine Chemicals AB, Uppsala, Sweden) in a centrifuge tube and the tube is centrifuged to obtain a mono-nuclear cell layer. To this mononuclear cell suspension, silica gel is added to remove macrophages, and lymphocytes are obtained. The lymphocytes are suspended in a culture medium supplemented with fetal calf serum to charge into nylon wool columns. The nylon wool columns adhering the lymphocytes are left to culture at 35°–38° C. for 30–45 minutes, and washed with the culture medium containing the same composition, and the lymphocytes are divided into nylon wool-adherent lymphocytes and nylon wool-passed lymphocytes. In the nylon wool-adherent lymphocytes, when the nylon wool and a culture medium previously cooled at 4° C. are contacted, mixed and shaken, the lymphocytes are detached into the culture medium from the nylon wool. Then, the medium is centrifuged.

Any type of nylon wool may be used. The preferred nylon wool is sold under the trademark LEUKO-PAK leukocyte filter (Fenwal Laboratories).

The obtained lymphocytes are suspended into a culture medium supplemented with fetal calf serum (containing penicillin and streptomycin in addition to L-glutamine and 2-mercaptoethanol). The obtained cell suspension is left to culture in an atmosphere of carbon dioxide at 35°–38° C. for 1–7 days. After culturing, the present factor is produced in the culture medium. The supernatant obtained by the centrifugation of the cultured cell suspensions is placed in a tube of dialysis membrane, and then the contents are sucked from outside and exuded to collect a dialysate. The present factors are contained in the dialysate, so that the dialysate can be used as it is, or as desired, the dialysate is then lyophilized and the augmenting factors for human antibody production are obtained as a powder.

The augmenting factors for human antibody production obtained in this process have physicochemical and biological properties as follows:

(1) Molecular weight of 2,000-4,000 [Elution before and after glucagon (molecular weight of 3,500) by a method of gel˙ filtration with the use of a gel filtration product trade named Sephadex G-50].

(2) Passage through a cellulose dialysis membrane (produced by Visking Company, having a diameter of 6 mm, a thickness of 0.0508 mm and a porosity diameter of 24A.)

(3) Stability at pH 2-11.

(4) Stability on heating at 30° C. for 60 minutes, at 56° C. for 30 minutes and at 100° C. for 2 minutes. Stability to six repetitions of freeze-thawing with freezing at −80° C. and thawing at 37° C.

(5) Inactivation on treatment with proteinase K (prepared by Boehringer Mannheim Co.) at 37° C. for 60 minutes. Stability to a treatment with ribonuclease A (RNase A, prepared by Boehringer Mannheim Co.) at 37° C. for 60 minutes.

(6)
(i) Augmentation and enhancement of the production of immunoglobulins, IgG and IgM by human lymphocytes.
(ii) Exhibition of no activity of T-cell growth factor (TCGF).
(iii) Exhibition of no activity of B-cell growth factor (BCGF).
(iv) Exhibition of no activity of B-cell differentiation factor (BCDF).

[Method of measuring activity]

Human peripheral blood or tonsil lymphocytes of $2 \times 10^5/100$ μl/well [containing Pokeweed mitogen (PWM) of 2 μl/200 μl] are placed on 96-well flat-bottom microplates, the present factor of 50 μl plus culture medium (RPMI-1640 culture medium supplemented with 15% fetal calf serum) of 50 μl, the present factor of 25 μl plus the culture medium of 75 μl and the present culture medium of 100 μl as a control medium ae added respectively into wells. The mixed suspensions are cultured in an atmosphere of 5% carbon dioxide at pH 7.2-7.4 for 7 days at 37° C. and centrifuged at 3,000 rpm for 10 minutes at 4° C. as these are placed on the microplates, and then the supernatants are collected. The amount of IgG/IgM (ng/ml) in the supernatants thus collected is measured by ELISA (enzyme-linked immunosorbent assay) method.

The activity of the present factors measured by the above method under several conditions is shown below.

[The amount of Immunoglobulin (Ig)]

| The present factors (μl/200μl) | IgG (ng/ml) Experiment 1* | Experiment 2* | IgM (ng/ml) Experiment 1* | Experiment 2* |
|---|---|---|---|---|
| 0% (0 μl) | 1,000 | 1,000 | 6,400 | 6,400 |
| 12.5% (25 μl) | 4,000 | 4,000 | 13,000 | 20,000 |
| 25% (50 μl) | 9,000 | 7,000 | 62,000 | 18,000 |

*In the experiments 1 and 2, the activity was measured after adding the present factors obtained from two different lots into lymphocytes prepared with the same tonsil.

[pH stability]

| | IgM (ng/ml) |
|---|---|
| Control | 7,200 |
| pH 2 | 7,800 |
| pH 11 | 8,100 |

Solutions of the present factors were prepared at pH 2 with 2N—HCl, and at pH 11 with 2N—NaOH, respectively. These solutions were left and neutralized. The activity was measured. As a result, the solutions were stable to both pH values.

| | IgM (ng/ml) |
|---|---|
| Heated the factors at 80° C., 60 minutes | 7,500 |
| Heated the factors at 56° C., 30 minutes | 11,000 |
| Heated the factors at 100° C., 2 minutes | 9,300 |
| Freeze-thawed the factors | 11,000 |
| Control | 7,200 |

The activity was measured after six times repetition of freezing at −80° C. with a freezer and thawing at 37° C. with warm water.

As mentioned above, the present factors are extremely stable on heating.

[Enzyme treatment]

| | IgM (ng/ml) | | IgG (ng/ml) | |
|---|---|---|---|---|
| | Experiment 1*** | Experiment 2*** | Experiment 1*** | Experiment 2*** |
| Proteinase K* treatment** | 200 | 100 | 800 | 900 |
| RNase A* treatment** | 800 | 950 | 5,400 | 6,300 |
| Control** | 600 | 750 | 5,600 | 5,500 |

*Prepared by Boehringer Mannheim Co.
**Each treatment was performed at 37° C. for 60 minutes, the control was treated similarly without adding enzymes.
***In the experiments 1 and 2, the factors obtained from two different lots were treated with enzyme and added into lymphocytes of peripheral blood, then the activity was measured.

As mentioned above, the factors of the present invention have excellent augmenting functions for human antibody production. The present factors can pass through a dialysis membrane, and can reduce the activity by the treatment of proteolytic enzyme (Proteinase K). Furthermore, the present factors are stable for RNase A treatment, heat and pH values in the usual range. The present factors are new augmenting factors for human antibody production completely different from conventional known augmenting factors for antibody production.

The ELISA method mentioned above is further described in Voller, Bidwell and Bartlett, Enzyme Immunoassays in Diagnostic Medicine. Theory and Practice, Bulletin of the World Health Organization, Vol. 53, pp. 55-65 (1976), incorporated herein by reference. The BCGF and BCDF factors mentioned above are further discussed in Okada et al, B Cell Growth Factors and B Cell Differentiation Factor From Human T Hybridomas. Two Distinct Kinds of B Cell Growth Factor and their Synergism in B Cell Proliferation, J. Exp. Med. Vol. 157, pp. 583-590 (1983), incorporated herein by reference.

The augmenting factors for human antibody production of the present invention may be prepared by a genetic engineering technique; namely, by recombinant DNA methods which integrate the factor production DNA with microbes, and also may be prepared by a cell hybrid technique, and may be prepared by established cell lines, so that the present factor prepared by these techniques are included in the scope of the present invention. Further discussions of these techniques may be found in Maniatis, T., E. F. Fritsch and J. Sambrook, Molecular Cloning: A Laboratory Manual. Cold Spring Harbor Laboratory, Cold Spring Harbor, N.Y., 1982; G. Köhler and C. Milstein. Continuous cultures of fused cells secreting antibody of predefined specificity, Nature 256, 495-497, 1975; and Monoclonal antibodies, Hybridomas: A New Dimension in Biological Analyses. Edited by R. H. Kennett, T. J. McKearn and K. B. Bechtol, 1980, all of which are incorporated by reference.

The present invention will be better understood from the following preferred example; however, the present invention is not limited to this example.

EXAMPLE

Two human tonsils were sliced into small pieces with a pair of curved scissors into an RPMI-1640 culture medium containing 1,000 U/ml of penicillin and 1,000 μg/ml of streptomycin, filtered through a gauze (100 mesh), to obtain tonsil cells. The tonsil cells were washed three times with a phosphate buffered saline at 4° C. for 10 minutes. The cells were separated by centrifuging at 1,500 rpm, respectively, and then suspended in 20 ml of an RPMI-1640 culture medium. Each suspension of about 3 ml thus obtained was placed on 2.5 ml of Ficoll-Paque (specific gravity 1.077) in six centrifuge tubes and the tubes were centrifuged at 2,200 rpm for 20 minutes at 18° C. A mononuclear cell layer was then separated. Each mononuclear cell layer of 2 ml was sucked up and to these cell suspensions 8 ml of a phosphate buffered saline was added, respectively. Each cell suspension was washed by centrifuging at 4° C. for 10 minutes, the first time at 1,800 rpm, and the second time and the third time at 1,500 rpm, respectively, and finally the mononuclear cells were obtained. The cells combined with the contents of these six centrifuge tubes were placed into a centrifuge tube (these six tubes were washed with a culture medium and the combined cells suspension was placed into the tube). The cells were suspended in an RPMI 1640 culture medium supplemented with 10% human AB serum. To the obtained cell suspension a silica suspension of 1/10 volume (a silica gel having a particle size of about 5 μm and suspended in 10% w/v of PBS. This silica gel is manufactured by Japan Antibody Research Laboratory.) was added and the mixture was incubated at 37° C. for 60 minutes with shaking by by every 15 minutes. (By this operation, macrophages in the mononuclear cells are removed by the silica). The cell suspension was placed on 2.5 ml of Ficoll-Paque and the tube was centrifuged at 2,200 rpm for 20 minutes at 18° C. to separate lymphocytes. The lymphocyte layer was sucked up and the obtained cell suspension was washed repeatedly with a phosphate buffered saline by centrifuging at 4° C. for 10 minutes, the first time at 1,800 rpm, and the second time and the third time at 1,500 rpm, respectively. The precipitated lymphocytes were suspended in 5 ml of an RPMI-1640 culture medium containing 10% fetal calf serum, and the cell suspension was poured into a nylon wool column (1 g of nylon wool was charged up to the position of 10 ml of an injector for 10 ml) (The nylon wool is sold under the trademark LEUKO-PAK leukocyte filter (Fenwal Laboratories). Fibers of the nylon wool are taken from a nylon wool column, disentangled or unraveled, and packed into the injector to be used.) previously washed by the same culture medium. The injector was laid as it was and was left to incubate at 37° C. for 30–45 minutes. The nylon wool column was washed with an RPMI-1640 culture medium supplemented with 10% fetal calf serum previously warmed to 37° C. (the flow rate was controlled by setting a needle of 19G to the head of an injector), and nylon wool-adherent lymphocytes and nylon wool-passed lymphocytes were separated. The nylon wool was taken out and put into a test tube. An RPMI-1640 culture medium cooled at 4° C. was added into the test tube. The contents were stirred well with a stick, and the nylon wool-adherent lymphocytes were detached from the nylon wool. Lymphocytes suspension was collected (about 40 ml), poured into another centrifuge tube and centrifuged at 1,500 rpm for 10 minutes at 4° C. The obtained nylon wool-adherent lymphocytes were suspended in an RPMI-1640 culture medium supplemented with 15% fetal calf serum (containing 2 mM of L-glutamine, $5 \times 10^{-5}$M of 2-mercaptoethanol, 100 units/ml of penicillin and 100 μg/ml of streptomycin). The suspended lymphocytes were dyed with Trypanblue (only dead cells were dyed) and counted only living cells by a blood cell counter, and the number of cells was adjusted to $2 \times 10^6$ cells/ml. This lymphocyte suspension was placed in a flask for tissue culture and the flask was left to culture at 37° C. for 5 days in a incubator containing 5% of carbon dioxide. After the culture, the cultured cell suspension was poured into a centrifuge tube, and centrifuged at 3,000 rpm for 15 minutes at 4° C. to obtain the supernatant liquid. A quantity (5 ml) of this supernatant was placed in a dialysis tube of cellulose dialysis membrane produced by the Visking Company and having a diameter of 6 mm, a thickness of 0.0508 mm and a porosity diameter of 24A, the tube was placed into a suction bottle, and the supernatant was sucked overnight. The culture medium passed through the dialysis membrane was passed into a milliporefilter (0.45 μm) for removing bacilli, and a dialysate containing the augmenting factors for human antibody production was obtained. The dialysate has a function for enhancing the above described IgG and IgM production. The dialysate was lyophilized and 10 mg of powdered proteins of the augmenting factors for human antibody production were obtained.

An augmenting range for human antibody production has an individual difference as a result of experiments obtained by separation of lymphocytes of 50 Japanese people. By adding the factors into a culture medium which produces IgG of 100–24,000 ng/ml/$2 \times 10^5$ of lymphocytes, Immunoglobulin (IgG) of 10,000–55,000 ng/ml/$2 \times 10^5$ of lymphocytes produces and augments. The augmented range is 2–10 times. By adding the factors into a culture medium which produces IgM of 10–7,500 ng/ml/$2 \times 10^5$ of lymphocytes, Immunoglobulin (IgM) of 20–65,000 ng/ml/$2 \times 10^5$ of lymphocytes produces and augments. The augmented range is 2–10 times.

The principles, preferred embodiments, and modes of operation of the present invention have been described in the foregoing specification. The invention which is to be protected herein, however, is not to be construed as limited to the particular forms disclosed, since these are to be regarded as illustrative rather than restrictive. Variations and changes may be made by those skilled in the art without departing from the spirit of the present invention.

What is claimed is:

1. Augmenting and enhancing factor for human antibody production wherein the factor is obtained from the supernatant of cultured human lymphocytes and the factor has physicochemical and biological properties as follows:
   (a) molecular weight of 2,000–4,000;
   (b) passage through a cellulose dialysis membrane having a diameter of 6 mm, a thickness of 0.0508 mm and a porosity diameter of 24A;
   (c) stability at pH 2–11;
   (d)
   (i) stability on heating at 30° C. for 60 minutes, at 56° C. for 30 minutes and at 100° C. for 2 minutes,
   (ii) stability to six repetitions of freeze-thawing with freezing at −80° C. and thawing at 37° C.;
   (e)
   (i) inactivation on treatment with proteinase K at 37° C. for 60 minutes,
   (ii) stability to a treatment with ribonuclease A at 37° C. for 60 minutes; and
   (f)
   (i) augmentation and enhancement of the production of immunoglobulins, IgG and IgM by human lymphocytes;
   (ii) exhibition of no activity of T-cell growth factor (TCGF);
   (iii) exhibition of no activity of B-cell growth factor (BCGF), and (iv) exhibition of no activity of B-cell differentiation factor (BCDF).

2. Augmenting and enhancing factors in accordance with claim 1, wherein the human lymphocytes are mononuclear cells obtained from tonsils, spleens, thymus or peripheral blood.

3. A process for preparing augmenting and enhancing factors for human antibody production from cultured human lymphocytes comprising: separating nylon wool-adherent human lymphocytes from nylon wool-passed human lymphocytes, culturing the nylon wool-adherent human lymphocytes, dialyzing the culture medium, and obtaining diffused dialysate through a dialysis membrane, said dialysate containing the augmenting and enhancing factors which factors have a molecular weight of about 2,000–4,000.

4. A process for preparing augmenting and enhancing factors in accordance with claim 3, wherein the human lymphocytes are mononuclear cells obtained from tonsils, spleens, thymus or peripheral blood of humans.

5. A process for preparing augmenting and enhancing factors in accordance with claim 3, wherein the nylon wool-adherent cells are cultured in a culture medium supplemented with fetal calf serum in an atmosphere of carbon dioxide and at a temperature of about 35°–38° C.

6. A process for preparing augmenting and enhancing factors in accordance with claim 3, further comprising lyophilizing the dialysate.

7. A process for preparing an augmenting and enhancing factor for human antibody production, comprising: obtaining mononuclear cells from human tonsils, separating lymphocytes from the mononuclear cells, suspending the obtained lymphocytes in a culture medium supplemented from fetal calf serum, adding the obtained lymphocyte suspension into a nylon wool column, eluting with the same culture medium to take off or remove nylon wool-passed lymphocytes to obtain nylon wool-adherent lymphocytes, washing off the nylon wool-adherent lymphocytes from the nylon wool, centrifuging the washed solution, suspending the obtained nylon wool-adherent lymphocytes into a culture medium supplemented with fetal calf serum, culturing the suspension in an atmosphere containing carbon dioxide and at a temperature of about 35°–38° C. for 1–7 days, centrifuging the cultured cell suspension to remove the lymphocytes, passing the obtained cultured cell supernatant through a dialysis membrane, obtaining diffused dialysate through a dialysis membrane containing the augmenting and enhancing factor which factors have a molecular weight of about 2,000–4,000, and lyophilizing the dialysate.

* * * * *